United States Patent [19]
Kucherov et al.

[11] 3,954,413
[45] May 4, 1976

[54] METHOD OF DETECTION OF CHROMATOGRAPHIC PEAKS

[76] Inventors: Viktor Fedorovich Kucherov, prospekt Vernadskogo, 97, korpus 1, kv. 13; Boris Antonovich Rudenko, ulitsa Fersmana, 13, kv. 21, both of Moscow; Margarita Alexandrovna Baidarovtseva, p/o Chernogolovka, poselok NNTS, ulitsa Pervaya, 34, kv. 11, Moskovskaya oblast, Noginsky raion, all of

[22] Filed: Nov. 29, 1974

[21] Appl. No.: 528,566

[52] U.S. Cl. .......................................... 23/254 EF
[51] Int. Cl.² .................................... G01N 31/12
[58] Field of Search ................. 23/254 EF; 73/23.1

[56] References Cited
OTHER PUBLICATIONS

Ackman et al., Anal. Chem. 35, 647 (1963).
Anal. Celestr. 15, No. 1083 (1968), Sucomalainen et al.
Tsuda et al., J. Chromatography 46, 241 (1970).
Klesper et al., J. Org. Chem. 27, 700 (1962).

*Primary Examiner*—Robert M. Reese
*Attorney, Agent, or Firm*—Haseltine, Lake & Waters

[57] ABSTRACT

A method of detection of chromatographic peaks in gas-liquid or gas-solid chromatography, comprising the ionization of the organic or metallo-organic compounds separated in a chromatographic column and removed in the form of fractions out of the column by an inert gaseous carrier. The ionization of the above compounds is effected by way of burning them in the flame of formic acid vapours. Simultaneously with the ionization, chromatographic peaks are recorded by means of the electrometric method based on measurement of the increase in the degree of the ionization of the flame as the above organic or metallo-organic compounds are being introduced thereinto.

3 Claims, 7 Drawing Figures

METHOD OF DETECTION OF CHROMATOGRAPHIC PEAKS

The present invention relates to methods of detection of chromatographic peaks in gas-liquid and gas-solid chromatography of organic and metallo-organic compounds.

A method is known in the art for the detection fo chromatographic peaks in gas-liquid or gas-solid chromatography, comprising the ionization of the organic or metallo-organic compounds separated in a chromatographpic column and removed in the form of fractions from the column by an inert gaseous carrier such as nitrogen, the ionization being effected by way of burning said compounds in the flame of a combustion gas, such as hydrogen, and accompanied by recording of the chromatographic peaks by the electrometric method and based on measurement of the increase in the degree of the ionization of the flame as said organic or metallo-organic compounds are being introduced thereinto.

The use of hydrogen as the combustion gas is disadvantageous in that:

1. hydrogen is highly explosive when mixed with air, thus necessitating special measures to be taken to ensure safety of the analysis, hence rendering the chromatographic apparatus more power-consuming, bulkier and heavier;

2. the use of high-pressure steel hydrogen cylinders as the source of hydrogen supply sharply increases the weight and size of the chromatographic apparatus, substantially complicates its maintenance, and involves additional hazards due to the presence in the apparatus of cylinders with highly explosive combustible gas compressed to a high pressure (150 to 300 atm);

3. the use of various electrolyzers as the source of hydrogen supply considerably complicates the structure of the chromatographic apparatus, renders it costlier, bulkier, more power-consuming and more difficult in its maintenance.

It is, therefore, an object of the present invention to provide a method of detection of chromatographic peaks in gas-liquid or gas-solid chromatography, free of the hazards involved in the use of hydrogen, which is highly explosive when mixing with air, without complicating the chromatographic apparatus used for the purpose and increasing its size, weight, power consumption and cost, as well as permitting detection to be comprehensive and highly sensitive.

With this and other objects in view, the invention resides in the ionization of the organic or metallo-organic compounds separated in a chromatographic column and removed, in the form of fractions, from the column by an inert gaseous carrier, the ionization being effected by way of burning said compounds in the flame of formic acid vapours and accompanied by the recordal of chromatographic peaks by the electrometric method based on measurement of the increase in the degree of the ionization of the flame as said organic or metallo-organic compounds are being introduced thereinto.

The use of formic acid, in the proposed method, as the combustible matter is advantageous because of the following considerations:

Formic acid, HCOOH, the simplest organic acid, is a colourless liquid with a boiling point of 101°C, an evaporation heat of 120 cal/g, a heat capacity of 0.525 cal/g and a saturated-vapour density at the boiling point of 0.0015 g/cu cm. A characteristic feature of formic acid, distinguishing it from the rest of the organic compounds, is the extremely low degree of ionization of its flame as it is being burned. This property of formic acid is due to the peculiarities of its molecular structure in which the only atom of carbon is bonded with two atoms of oxygen. Therefore, the combustion of formic acid in air, in accordance with the equation

$$HCOOH + \tfrac{1}{2} O_2 \rightarrow H_2O + CO_2,$$

does not involve any appreciable formation of free electrons or any other electrically charged particles, in contrast to the combustion of other organic substances (cf. P. Bocek and J. Janak, Chromatographic Reviews, 15, 111/1971).

When, into the flame of formic acid vapours, are introduced organic and metallo-organic compounds which are richer in carbon content, the degree of ionization of the flame sharply increases, the increase of which can be easily recorded by the electrometric method.

Thus, the proposed method of detection of chromatographic peaks permits the avoidance of the use of an explosive gas, such as compressed hydrogen, hydrogen being substituted by formic aicd. This substitution in no way affects the high sensitivity and comprehensiveness of detection. Dispensing with compressed hydrogen cylinders permits cutting down appreciably the size and weight of the chromatographic apparatus. The low heat of evaporation of formic acid accounts for insignificant energy consumption involved in the conversion of formic acid to its vapours. The energy thus consumed constitutes but a minor amount of the energy required, for example, to obtain an equivalent amount of hydrogen by electrolysis of water. The low density of formic acid vapours accounts for modest consumption thereof in chromatographic peak detection by the proposed method, namely, 1 to 4 ml of liquid formic acid per hour. These advantages of the propose method make it possible to create light, highly efficient chromatographic analyzers characterized by low power consumption, including portable ones convenient for in-the-field, on-vehicle, on-line and other uses.

The herein disclosed method of detection can advantageously be applied in packed analytical column, preparative and capillary techniques of gas chromatography.

Used as the inert gaseous carrier in this method can be such gases as nitrogen, helium, argon, carbon dioxide, sulphur dioxide, as well as vapours of water, formic acid, perchlorofluorocarbons, sulphur hexafluoride or carbon disulphide.

When formic acid vapours are employed as the gaseous carrier, the latter may be used as the combustible matter, as it emerges from the chromatographic column. This feature eliminates the necessity of separately feeding a combustible matter into the detector, thereby substantially simplifying the structure of the chromatographic apparatus.

It should be noted at this point that by an inert gaseous carrier is meant a mobile agent which transfers the vaporous or gaseous substances being separated along the chromatographic column and, chromatographic separation being over, into the detector. This mobile agent does not enter into chemical reactions with the material of the chromatographic column, material of the conduits, column packing material, substances being separated or combustible matter (formic acid vapours).

The invention will now be described in greater detail with reference to an embodiment thereof, taken in conjunction with the accompanying drawings, in which.

Figure 6:
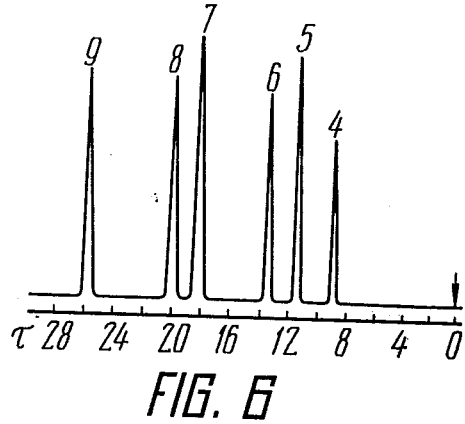
Figure 7:
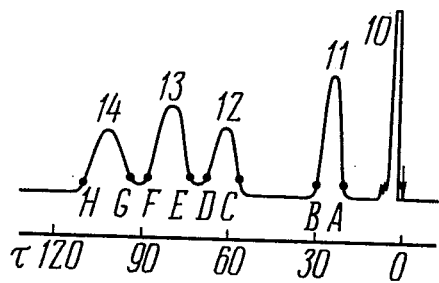

FIG. 6 is a gas-liquid chromatogram of terpenes ($\alpha$-pinene, camphene, $\beta$-pinene, myrcene, dipentene, $\gamma$-terpinene), obtained on a capllillary column in a flow of nitrogen with the aid of a flame ionization detector using the flame of formic acid vapours; and FIG. 7 is a gas-liquid chromatogram of preparatively separated aromatic hydrocarbons (triphenylene, ortho-, meta- and para-terphenyls), obtained in a flow of water vapours with the aid of a flame ionization detector using the flame of formic acid vapours.

The proposed method of detection of chromatographic peaks in gas-liquid or gas-solid chromatography is carried out as follows.

Organic or metallo-organic compounds, previously separated in a chromatographic column and eluted, in the form of fractions, from the column by an inert gaseous carrier, are carried with the flow of said carrier into a flame ionization detector. The latter comprises a burner for burning formic acid vapours and electrodes for measuring the degree of intensification of the flame ionization. At the same time, formic acid vapours are directed to the burner in a flow, to stabilize the flame. Formic acid vapours are obtained either by boiling liquid formic acid in an evaporator with the resulting vapours being directed to the burner of the detector, or by forcing liquid formic acid, e.g. by means of a pump, through a pipe coil heated to a temperature exceeding the boiling point of formic acid, with the resulting vapours being directed to the burner of the detector.

The degree of intensification of the ionization of the flame, occurring while the separated organic or metallo-organic compounds are being burnt in formic acid vapours, is recorded by means of an electrometer comprising a d-c amplifier and an output electrical measuring recording means, for example, a potentiometric recorder.

When formic acid vapours are used as the inert gaseous carrier, they are fed into the chromatographic column in a flow which is in conformity with the requirements of a chromatographic analysis. As the formic acid vapours containing fractionated organic or metallo-organic compounds are eluted from the column, they are carried to the burner of the detector. In this case, feeding formic acid vapours into the burner in a separate flow is not necessary.

For a better understanding of the present invention, it will now be illustrated by the following examples.

EXAMPLE 1

A mixture of saturated aliphatic $C_6$–$C_{10}$ alcohols in an amount of 0.2 mg, were separated by the gas-liquid chromatography technique on a column 1 m long and 0.4 cm in diameter, packed with Chromosorb W (manufactured by Johns-Manville, a U.S. company) containing 10 wt % of polyethylene glycol having a molecular weight of 6,000, in a flow of nitrogen (flow rate: 40 ml/min), the column temperature being 80°C. At the same time, a flow of formic acid vapours was fed into a flame ionization detector (flow rate: 80 to 100 ml/min) from a vapour generator having a capacity of 100 ml, containing 50 to 70 ml of liquid formic acid and accommodated in a heater in which a temperature of 125°C was maintained.

Chromatographic peaks were recorded with the aid of a conventional electrometric means, the voltage across its electrodes being 200 V, the gain factor of its amplifier being 1,000 and the sensitivity of its recording potentiometric recorder being 10 mV.

Figure 1:
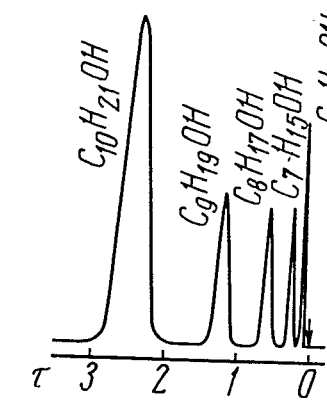
FIG. 1 is a gas-liquid chromatogram of a mixture of saturated aliphatic $C_6$–$C_{10}$ alcohols, obtained in a flow of nitrogen and recorded with the aid of a flame ionization detector using the formic acid vapour flame.

The chromatogram obtained under the above conditions is shown in FIG. 1 with the retention times of the component separated being plotted along the axis $\tau$, in minutes.

The fitness of the recorded chromatographic peaks to the Gaussian curve was checked by the linearization method (cf. B. A. Rudenko, E. L. Ilkova and S. Ya. Metlyaeva, Analiticheskaya khimiya, 25, No. 4,670, 1970). The check revealed that the recorded peaks are in a full agreement with the Gaussian curve. This agreement corroborates the fact that the detecting system used in the analysis does not introduce any errors as the concentration of the fraction emerging from the column is being converted into an electric signal, as well as while this signal is being recorded.

Calculated for decyl alcohol peak, shown in FIG. 1, the sensitivity of the detector, according to Dimbat, Porter and Stross (cf. M. Dimbat, P. E. Porter and F.H. Stross, Anal. Chem., 28, 290, 1956), was F. H. to $1.2 \cdot 10^4$ mV·ml/mg, this sensitivity being not inferior to that of a hydrogen flame ionization detector used in a system incorporating a packed analytical column similar to the one employed in this Example.

To qualify the dependence of the magnitude of the detector response signal on the amount of the substance being introduced into the detector, a series of chromatographic analyses were conducted under the above-described conditions by varying the amount of the decyl alcohol in the mixture being chromatographed from 0.01 to 0.07 mg. The graph constructed on the basis of the results obtained from this series of analyses, shown in FIG. 1, is indicative of the fact that the dependence of the detector response signal mangitude (S) on the amount (g) of the decyl alcohol being detected is linear. This is in keeping with the graphs showing the magnitude of the signal of a hydrogen flame ionization detector versus the amount of the components being detected that are known at present.

This example demonstrates the suitability of the proposed method for detecting chromatographic peaks of organic compounds separated by the analytical column gas-liquid chromatography employing packed analytical column technique with nitrogen used as the carrier gas.

EXAMPLE 2

0.03 mg of a mixture of aromatic hydrocarbons (benzene, toluene and m-xylene) were separated by the gas-solid chromatography technique in a flow of nitrogen (flow rate: 80 ml/min) on a column 1 m long and 0.3 cm in diameter, packed with graphitized carbon black, at a temperature of 90°C. Simultaneously, a flow of formic acid vapours (flow rate: 40 ml/min) was fed into a flame ionization detector, said flow being obtained by evaporating, at a rate of 3 ml/h, liquid formic acid in an evaporator coil heated to 120°C.

Chromatographic peaks were recorded with the aid of the electrometric means of Example 1 with the difference that the sensitivity of its potentiometric recorder was in 50 mV in this case.

Figure 3:
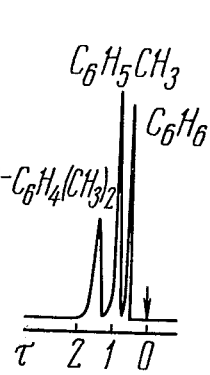
FIG. 3 is a gas-solid chromatogram of a mixture of aromatic hydrocarbons (benzene, toluene and m-xylene), obtained in a flow of nitrogen and recorded with the aid of a flame ionization detector using the formic acid vapour flame.

The chromatogram obtained under these conditions is represented in FIG. 3 with the retention times being plotted along the axis $\tau$, in minutes.

Calculated with respect to a m-xylene peak, shown in FIG. 3, the sensitivity of the detector equalled $1.8 \cdot 10^4$ mV. ml/mg, this sensitivity being not inferior to that of a hydrogen flame ionization detector used in a system incorporating a similar packed analytical column.

This example shows that the proposed method can be advantageously used for the detection of chromatographic peaks of organic compounds separated by the analytical column gas-solid chromatography technique in nitrogen carrier-gas flow.

EXAMPLE 3

A mixture of metallo-organic compounds (hexafluoroacetylacetonates of iron and chromium), in an amount of 0.1 mg and dissolved in acetone (concentration of the solution: 10 wt %), was separated by the gas-liquid chromatography technique in a flow of helium as the carrier gas (flow rate: 80 ml/min) on a column 0.5 m long and 0.4 cm in diameter, packed with Chromaton (manufactured by "Lachema", Czechoslovakia) containing 10 wt % of polyethylene glycol having a molecular weight of 6,000, at a temperature of 100°C. At the same time, a flow of formic acid vapours was introduced into a flame ionization detector (flow rate: 100 to 150 ml/min) from a steam generator with a capacity of 150 ml, containing 100 to 200 ml of liquid formic acid and accommodated in a heater wherein a temperature of 125°C was maintained.

Chromatographic peaks were registered with the aid of the electrometric means of Example 2.

Figure 4:
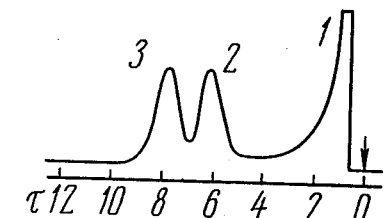
FIG. 4 is a gas-liquid chromatogram of metallo-organic compounds (hexafluoro acetylacetonates of iron and chromium), obtained in a flow of helium with the aid of a flame ionization detector using the flame of formic acid vapours.
Figure 2:
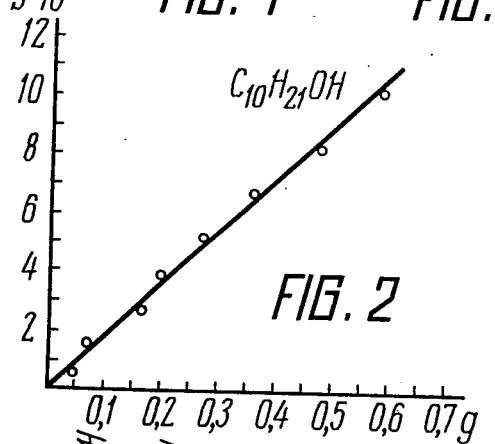
FIG. 2 is a graph showing the magnitude of the detector signal versus the amount of decyl alcohol eluted from the column into the detector, constructed in coordinates S-g. S is the magnitude of the detector signal, expressed as the area of the recorded peak, in mV.sec, and g is the amount of the decyl alcohol being fed from the column into the detector, in mg.

The chromatogram obtained under the above conditions is shown in FIG. 4 with the retention times being plotted along the axis $\tau$, in minutes. In this graph, chromatographic peak 1 corresponds to acetone, peak 2 corresponds to chromium hexafluroacetylacetonate, and peak 3 corresponds to iron hexafluoroacetylacetonate.

Calculated with respect to peak 3 representative of iron hexafluoroacetylacetonate (FIG. 4), the sensitivity of the detector was equal to $1.1 \cdot 10^4$ mV.ml/mg, which corresponds to the sensitivity of a hydrogen flame ionization detector used in a system including a similar packed analytical column This example shows that the proposed method is fully applicable for the detection of chromatographic peaks of metallo-organic compounds separated by the packed analytical column gas-liquid chromatography technique in a flow of helium, as the carrier gas.

EXAMPLE 4

A mixture of free saturated aliphatic acids $C_6$–$C_{14}$, taken in an amount of 0.4 mg, was separated by the gas-liquid chromatography technique in a flow of formic acid vapours (flow rate: 60 ml/min) on a column 2 m long and 4 mm in diameter, packed with Chromaton (manufactured by Lachema, Czechoslovakia) containing 10 wt % of polysiloxane elastomer SE-30 (manufactured by General Electric Co., a U.S. firm), at a temperature of 220°C. Formic acid vapours were fed into the column from a vapour generator having a capacity of 100 ml, containing 50 to 70 ml of liquid formic acid and accommodated in a heater in which a temperature of 150°C was maintained. The pressure in the vapour generator was 0.5 atm.

The formic acid vapours emerging from the column and containing the separated components were directed to the burner of a detector. No additional formic acid vapours were introduced into the detector.

Chromatographic peaks were recorded with the aid of the electrometric means of Example 2.

Figure 5:
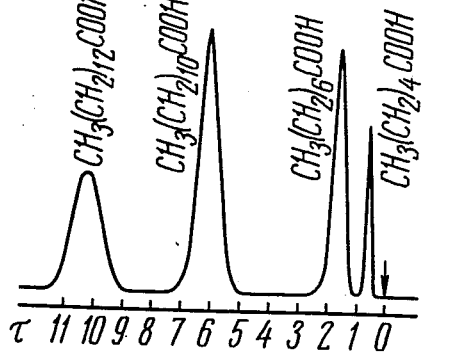
FIG. 5 is a gas-liquid chromatogram of free saturated aliphatic acids $C_6$–$C_{14}$, obtained in a flow of formic acid vapours and recorded with the aid of a flame ionization detector using the flame of formic acid vapours.

The chromatogram obtained under these conditions is represented in FIG. 5 with the retention time being plotted along the axis $\tau$, in minutes.

Calculated with respect to a peak of lauric acid, shown in FIG. 5, the sensitivity of the detector was equal to $6 \cdot 10^4$ mV·ml/mg which is a rather high value for an analysis with packed columns.

This example makes it clear that the proposed method is fully applicable for the detection of chromatographic peaks of organic compounds separated by the packed analytical column gas-liquid chromatography technique in a flow of formic acid vapours.

EXAMPLE 5

A mixture of terpenes ($\alpha$-pinene, camphene, $\beta$-pinene, myrcene, dipentene and $\gamma$-terpinene) was separated by the capillary gas-liquid chromatography technique in a flow of nitrogen using a copper capillary column 50 m long and 0.25 mm in diameter, coated with dinonylphthalate. The column temperature was 120°C and the nitrogen pressure at the column inlet was 1.5 atm. The mixture of terpenes was introduced into a chromatograph in an amount of 0.1 mg. The mixture was evaporated in a flow of a carrier gas with 0.1% of the total gas flow being directed into the column and 99.9% of the gas being vented to the atmosphere. Thus, a thousandth part of the terpene mixture initially introduced into the chromatograph was fed into the chromatographic column.

The terpenes separated in the column were removed therefrom by a flow of nitrogen and directed into a detector. At the same time, a flow of formic acid vapours was fed into the detector at a rate of 15 ml/min, this rate corresponding to the rate of 1 ml/h at which liquid formic acid was fed into an evaporator coil. The temperature in the evaporator coil heater was 120°C.

The chromatogram thus obtained is shown in FIG. 6 with the retention time being plotted along the axis $\tau$, in minutes. In this graph, chromatographic peak 4 corresponds to $\alpha$-pinene, peak 5 corresponds to camphene, peak 6 corresponds to $\beta$-pinene, peak 7 corresponds to myrcene, peak 8 corresponds to dipentene, and peak 9 corresponds to $\gamma$-terpinene.

Calculated with respect to the total area of the chromatogram of FIG. 6, the sensitivity of the detector was equal to $1.3 \cdot 10^6$ mV.ml/mg, this sensitivity corresponding to that of a hydrogen flame ionization detector incorporated in a system using a similar capillary column.

This example suggests that the proposed method can successfully be applied for the detection of chromatographic peaks in capillary column gas chromatography.

EXAMPLE 6

0.3 g of a mixture of high-boiling aromatic hydrocarbons (triphenylene, ortho-, meta- and para-terphenyls, dissolved in benzene (concentration of the solution: 20 wt %), were separated by the preparative -scale gas-liquid chromatography on a column 3 m long and 15 mm in diameter, packed with Chromaton (manufactured by Lachema, Czechoslovakia) containing 10 wt % of polysiloxane elastomer SE-30 (manufactured by General Electric Co., a U.S. firm). The temperature at the column was 210°C, and the pressure of the mobile carrier, water vapours, at the column inlet was 0.8 atm.

1% of the water vapours emerging from the column and containing a respective amount of the separated fractions was directed into a flame ionization detector. Simultaneously, fed into the detector was a flow of formic acid vapours at a rate of 30 ml/min, this rate corresponding to the rate of 2.5 ml/h at which liquid formic acid was fed into an evaporator coil. The temperature in the evaporator coil was maintained equal to that at the column.

Chromatographic peaks were recorded with the aid of the electrometric means of Example 2, the separated fractions of the hydrocarbons being collected in accordance with the detector read-out.

The chromatogram obtained under the above-specified conditions is shown in FIG. 7 with the points of sampling of the separated fractions being indicated therein and the time consumed by the chromatographic analysis being plotted along the axis $\tau$, in minutes. In the graph represented in FIG. 7, chromatographic peak 10 corresponds to benzene, peak 11 corresponds to triphenylene, peak 12 corresponds to ortho-terphenyl, peak 13 corresponds to metaterphenyl, peak 14 corresponds to para-terphenyl. The points of sampling of the separated fractions are designated as follows:

A — point of the beginning of the triphenylene fraction collecting;
B — point of the end of sampling of the triphenylene fraction;
C — point of the beginning of the ortho-terphenyl fraction collecting;
D — point of the end of the ortho-terphenyl fraction collecting;
E — point of the beginning of the meta-terphenyl fraction collecting;
F — point of the end of the meta-terphenyl fraction collecting;
G — point of the beginning of the para-terphenyl fraction collecting;
H — point of the end of the para-terphenyl fraction collecting.

Calculated with respect to the total area of chromatographic peaks 11, 12, 13 and 14 of the chromatogram of FIG. 7, the sensitivity of the detector was equal to $2 \cdot 10^4$ mV·ml/mg this sensitivity corresponding to that of a hydrogen flame ionization detector incorporated in a system using a similar preparative column.

The purity of the collected fractions was checked by a gas-chromatographic analysis. This analysis has revealed a total absence of mutual contamination of the above-mentioned fractions, which is indicative of the absence of response lags or other faults in the detecting system.

This example points to the fact that the proposed method is equally applicable for the detection of chromatographic peaks of organic compounds separated by the preparative scale gas chromatography technique.

Examples 1-6 provide a convincing proof of the versatility of the proposed method of detection of chromatographic peaks and its applicability in the separation of organic and metallo-organic compounds both in gas-solid and in gas-liquid chromatography, in a flow of conventional gases as well as vapours of volatile substances.

These examples leave no doubt as to the applicability of the proposed method in packed analytical column, capillary and preparative scale techniques of gas chromatography. They equally corroborate the feasibility of this method in cases where a hydrogen flame ionization detector is normally used.

What is claimed is:

1. A method of detection of chromatographic peaks in gas-liquid or gas-solid chromatography, consisting in the ionization of compounds selected from the group consisting of organic and metallo-organic compounds, said compounds being cut prior to the ionization in a chromatographic column and removed, in the form of fractions, from said column by an inert gaseous carrier, the ionization of said compounds being effected by way of burning them in the flame of formic acid vapours and accompanied by recording of chromatographic peaks by an electrometric method based on measurement of the increase in the degree of the ionization of the flame as said compounds are being introduced thereinto.

2. A method as claimed in claim 1, wherein said inert carrier gases are nitrogen, helium, argon, carbon dioxide or sulphur dioxide.

3. A method as claimed in claim 1, wherein said inert carrier gases are vapours of water, formic acid, perchlorofluorocarbons, sulphur hexafluoride or carbon disulphide.

* * * * *